US011344445B2

(12) United States Patent
Garriga I Rodo

(10) Patent No.: US 11,344,445 B2
(45) Date of Patent: May 31, 2022

(54) HYGIENIC DEVICE FOR THE COLLECTION OF MENSTRUAL FLOW

(71) Applicant: ECAREYOU INNOVATION, S.L., Rubi (ES)

(72) Inventor: Joan Garriga I Rodo, Rubi (ES)

(73) Assignee: ECAREYOU INNOVATION, S.L., Rubi (ES)

(*) Notice: Subject to any disclaimer, the term of this patent is extended or adjusted under 35 U.S.C. 154(b) by 825 days.

(21) Appl. No.: 16/308,603

(22) PCT Filed: Jun. 2, 2017

(86) PCT No.: PCT/ES2017/070402
§ 371 (c)(1),
(2) Date: Mar. 27, 2019

(87) PCT Pub. No.: WO2017/212094
PCT Pub. Date: Dec. 14, 2017

(65) Prior Publication Data
US 2019/0224039 A1  Jul. 25, 2019

(30) Foreign Application Priority Data
Jun. 10, 2016 (ES) .............................. ES201630767U

(51) Int. Cl.
*A61F 5/455* (2006.01)
*A61F 5/44* (2006.01)
(52) U.S. Cl.
CPC .......... *A61F 5/4553* (2013.01); *A61F 5/4404* (2013.01)
(58) Field of Classification Search
CPC combination set(s) only.
See application file for complete search history.

(56) References Cited

U.S. PATENT DOCUMENTS 3,102,541 A * 9/1963 Adams .................. A61F 5/4553
 604/15
3,128,767 A * 4/1964 Nolan ....................... A61F 6/08
 604/330

(Continued)

FOREIGN PATENT DOCUMENTS

CN  203634351 U  6/2014
DE  202006013346 U1  10/2006

(Continued)

OTHER PUBLICATIONS

International Search Report dated Aug. 22, 2017 for International Application No. PCT/ES2017/070402 filed Jun. 2, 2017.

*Primary Examiner* — Guy K Townsend
(74) *Attorney, Agent, or Firm* — Blue Filament Law PLLC

(57) ABSTRACT

A hygienic device for the collection of menstrual flow includes an impermeable and flexible body (2), that is receptacle-shaped, cup type, in which lower external part, the opposite to the mouthpiece (21), fastening means (3) to proceed to its withdrawal after it is used. The fastening means (3) includes a threadlike element (31). Eventually, the threadlike element (31) has a structure easy to be cut by one, two or more points (32), so that the user can cut it at will until leaving it with a minimum length. Eventually, the threadlike element (31) possesses, in the proximal area, at least, one protrusion (33) and at the distal end of the threadlike element (31) it possesses a protrusion (33). Eventually, at the upper part of the body (2) of the receptacle one or more holes (4) have been provided close to the edge of the mouthpiece (21).

7 Claims, 1 Drawing Sheet

(56) References Cited

U.S. PATENT DOCUMENTS

| | | | | |
|---|---|---|---|---|
| 3,626,942 A * | 12/1971 | Waldron | ............... | A61F 6/08 604/330 |
| 4,961,436 A * | 10/1990 | Koch | ............... | A61F 6/08 128/834 |
| 5,295,984 A * | 3/1994 | Contente | ............... | A61F 5/4553 604/327 |
| 5,827,248 A * | 10/1998 | Crawford | ............... | A61F 5/4553 604/328 |
| 6,168,609 B1 * | 1/2001 | Kamen | ............... | A61F 5/4553 600/573 |
| 6,264,638 B1 * | 7/2001 | Contente | ............... | A61M 31/002 604/285 |
| 8,454,493 B2 * | 6/2013 | La Vean | ............... | A61F 6/08 600/33 |
| 2002/0143303 A1 * | 10/2002 | Intravartolo | ............... | A61F 6/08 604/385.18 |
| 2008/0077097 A1 * | 3/2008 | Chambers | ............... | A61F 5/4553 604/330 |
| 2008/0200888 A1 * | 8/2008 | Gooch | ............... | A61F 5/4553 604/330 |
| 2010/0312204 A1 * | 12/2010 | Sheu | ............... | A61F 5/4408 604/330 |
| 2014/0012216 A1 * | 1/2014 | Shaviv | ............... | A61F 5/4553 29/428 |
| 2016/0278988 A1 * | 9/2016 | Knox | ............... | A61F 5/4553 29/428 |

FOREIGN PATENT DOCUMENTS

| WO | WO-2006058409 A1 * | 6/2006 | ............ A61F 5/4553 |
|---|---|---|---|
| WO | 2007082341 A1 | 7/2007 | |
| WO | WO-2007082341 A1 * | 7/2007 | ............ A61F 5/4553 |

* cited by examiner

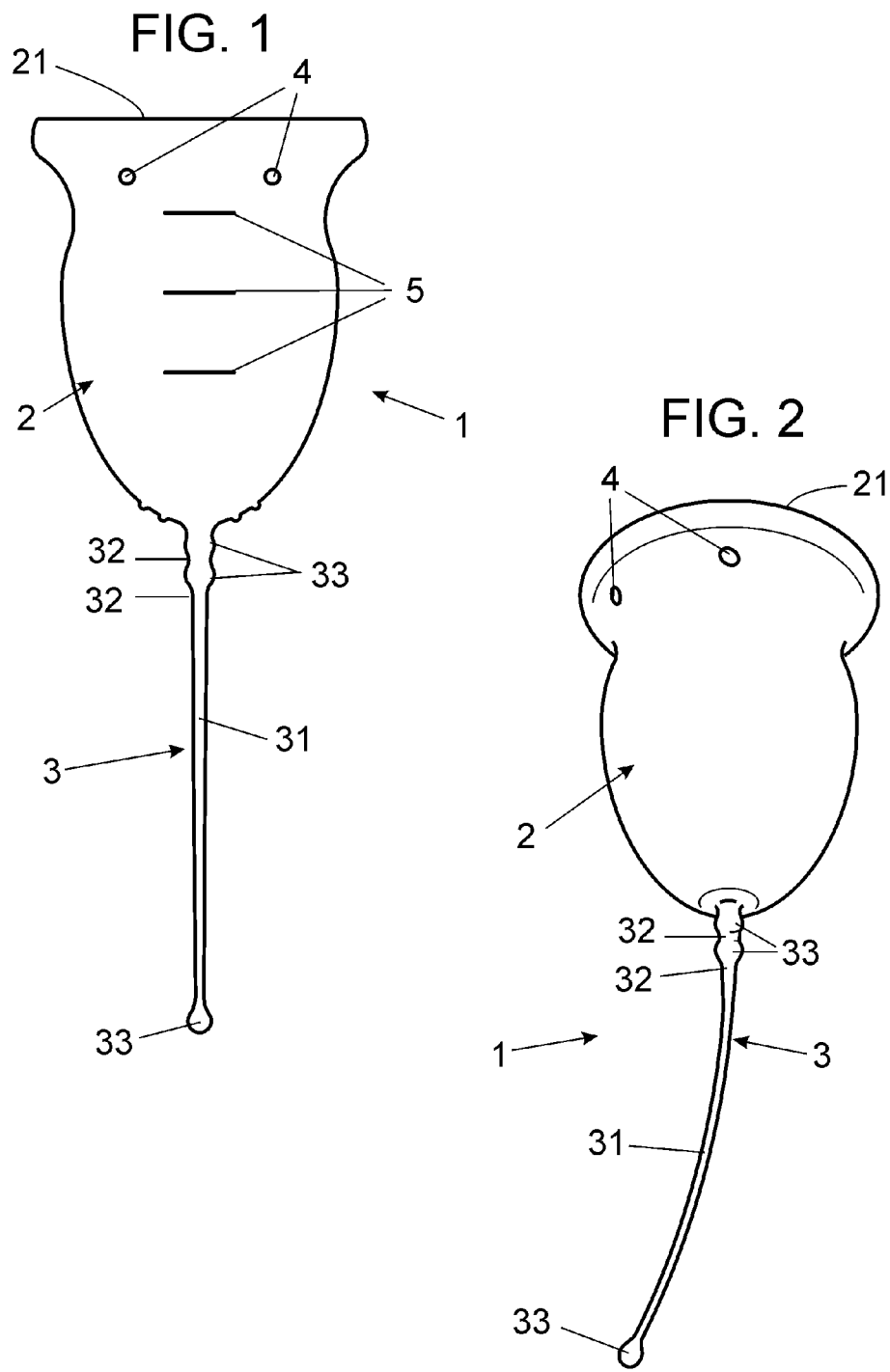

HYGIENIC DEVICE FOR THE COLLECTION OF MENSTRUAL FLOW

OBJECT OF INVENTION

The invention, as stated in the title of this specification, refers to a hygienic device for collecting menstrual flow, that contributes, to the function to which it is designed, with advantages and characteristics of novelty that will be disclosed in detail thereafter, that mean an improvement to the current state-of-art in its field of application.

The object of this invention refers to a menstrual device that, being of the type known in the sector as "menstrual cup" and constituted by a body of impermeable and flexible material, for example silicone, receptacle-shaped and designed to be placed in the woman vagina to collect the menstrual flow, is distinguished for having an improved structural configuration with respect to other similar devices existing in the market, mainly focused in its withdrawal means after it is used, that provides significant advantages for the users, namely for who is starting to use this type of devices, because it facilitates and secures an easy and quick withdrawal.

FIELD OF APPLICATION OF THE INVENTION

The field of application of this invention is within the sector of the industry engaged in producing articles of woman intimate hygiene, particularly focusing on the scope of those designed to containment of the menstrual flow, and more particularly on those known as menstrual cups.

BACKGROUND OF THE INVENTION

As reference to the current state-of-art, it shall be pointed out that this type of devices is very well-known in the market, the use of which, although relatively recent, is every time more extended because of the advantages it provides, above all hygienic, compared with other systems of containment of the menstrual flow, such as tampons, sanitary napkins and the like.

However, its use poses certain reticences, specially in new users, because of the difficulty meant by its withdrawal and, at same time, for fear that the cup could remain lost within the body.

In general, the menstrual device or cup, as pointed out before, is constituted from a receptacle-shaped body, that looks like the shape of a cup (hence its name) made of a flexible and impermeable material, normally silicone, which, at its lower part, that means, the opposite to its mouthpiece, has a small thickening, normally spherical, that serves as fastening point to proceed to withdrawing the cup from within the vagina, after it is used.

Now, modifying the fastening system is the problem that this invention seeks to improve, because the above-mentioned thickening, as it is small, remains located within the body and, namely for the new users, that means a handicap that poses reticences as they do not know whether the cup could be lost within the body and because it does not facilitate the withdrawal.

On the other hand, although, as it was said, the devices of the type involved herein are known, the existence of no one is known having technical or structural characteristics equal or similar to those that the device herein claimed possesses.

EXPLANATION OF THE INVENTION

The hygienic device for collecting the menstrual flow proposed by the invention is therefore configured as a novelty within its field of application, because when implementing it, the stated objectives are satisfactorily met, the characterizing details making it possible and distinguishing it duly appearing in the final claims attached to this description.

Concretely, what is proposed by the invention, as above stated, is a menstrual device of the type known as "menstrual cup" that is constituted by a body of impermeable and flexible material, for example silicone, receptacle-shaped similar to a cup, and that is designed to be placed in the woman vagina for collecting the menstrual flow, in which external lower part, the opposite to the mouthpiece, fastening means have been provided to proceed to its withdrawal after it is used.

From this already known configuration, the device of this invention is essentially distinguished, by the fact that the said fastening means for the withdrawal of the device comprise a threadlike element, consisting, for example, in a length of string or, preferably, in a long and thin extension of the material itself of which the body of the receptacle is made. Anyway, with a sufficient length in order that, once the device has been placed, its distal end remains located external to the vagina.

With this it is achieved that the user, on the one hand, feels safe and avoid thinking in the possibility to have the cup lost within her body, and on the other hand, the withdrawal of the device is much easier for her.

The said threadlike element, in addition, according to the characteristics of the invention, has the peculiarity to be easily cut, preferably at, at least, two points, so that the user, using a suitable tool for it, for example scissors, as it is designed so that it does not break when pulling it with the use, can cut it while gaining more assertiveness in the use of the device until being able to use it with a minimum length.

For this, the said threadlike element has, in the proximal area, that means that joining it to the lower part of the body of the receptacle, at least, a protrusion and, preferably, two protrusions separate by a recess, that will serve as fastening point after cutting the rest of the threadlike element, it can be chosen, depending on the preference of the user, to leave both or only the one more proximal of the said protrusions.

It shall be likewise pointed out that, in the preferred embodiment, the distal end of the said threadlike element has also a third protrusion, in this case to facilitate fastening the threadlike body when the device is used without it having been cut.

In addition, the body of the receptacle has, at its upper part, close to the mouthpiece, at least a hole, although preferably, two or three holes, horizontally aligned are included, which aim is to be able to break the void when the device is used and, as it is close to the edge, the no leakage of the flow is best secured when the receptacle is full.

Last, the hygienic device for collecting the menstrual flow of the invention is produced in different sizes, preferably, three having different diameters in the cup-shaped receptacle and different lengths of the threadlike element to facilitate the withdrawal, adapted to the different needs of the users.

The hygienic device disclosed for collecting the menstrual flow consists, therefore, of an innovating structure having characteristics unknown up to now for the purpose to which it is designed, reasons that jointly to its practical utility, provide it with sufficient foundation to obtain the privilege of exclusivity applied for.

DESCRIPTION OF THE DRAWINGS

To complement the description carried out and in order to assist to best understand the characteristics of the invention, attached to this specification, as an integral part thereof, is a sheet of drawings in which, for illustration and no limitation purpose, the following has been represented:

FIG. 1.—It shows an elevation view of a hygienic device for collecting the menstrual flow, object of the invention, the parts and elements it comprises can be seen, as well as its configuration and arrangement; and FIG. 2.—It shows a view in perspective of the same example of the device of the invention shown in the FIG. 1.

PREFERRED EMBODIMENT OF THE INVENTION

Seen the figures disclosed, and according to the numerals adopted in them, a non-limiting example of device of the invention can be seen, which comprises the parts and elements that are indicated and disclosed in detail below.

Thus, as it can be seen in the said figures, the device (1) involved comprises, in an already known manner, an impermeable and flexible body (2), for example of silicone, a cup-shaped receptacle, in which lower external part, the opposite to the mouthpiece (21), it possesses fastening means (3) to proceed to its withdrawal after it is used, distinguished in that the said fastening means (3) comprise a threadlike element (31), consisting, for example, in a length of string or, preferably, in a long and thin extension of the material itself of which the body of the receptacle is made, having a sufficient length in order that, once the device (1) is placed in the body of the user, its distal end remains externally located.

The said threadlike element (31), in addition, has a structure that can be easily cut, using a suitable cutting tool, by one, two or more points (32), so that the user can cut it at will until leaving it with a minimum length.

For this, in the preferred embodiment, the threadlike element (31) has, at the proximal area, that joining it to the lower part of the body (2) of the receptacle, at least, a fastening protrusion (33) when breaking or cutting the threadlike element by the breaking point (32) that leaves it at its minimum length, although, preferably, it has two protrusions (33) separate by a recess that, optionally, also constitutes a breaking or cutting point (32) of those precedingly disclosed.

Anyway, also in a preferred manner, the distal end of the threadlike element (31) also has a protrusion (33), in this case to facilitate fastening the threadlike body when it is complete.

Last, at the upper part of the body (2) of the receptacle one or more holes (4) have been provided arranged close to the edge of the mouthpiece (21), horizontally aligned when there is more than one, that means, parallel to the said edge of the mouthpiece (21), with the aim of breaking the void when the device is used avoiding at same time the leakage of the flow through it when the receptacle is full.

In addition, at the external part of the body (2) of the receptacle, several marks (5) have been provided indicating the capacity of the content the said receptacle has.

Sufficiently disclosed the nature of this invention, as well as the manner of implementing it, it is not deemed necessary to extend any more the explanation in order that any man skilled in the art understands its scope and the advantages arising from it, and it is stated, within its essence, that it can be implemented in other embodiments that differ in detail of that indicated for example purpose, and to which the protection sought is applied for is extended, provided that its fundamental principle is not altered, changed or modified.

The invention claimed is:

1. A hygienic device for the collection of menstrual flow, comprising:
    an impermeable and flexible body (2) having a receptacle-shaped, cup type, form and formed of an impermeable and flexible material; the flexible body (2) comprising:
        an external lower part opposite to a mouthpiece (21);
        a fastening means (3) capable of being used for withdrawal after use;
        said fastening means (3) comprising:
            a threadlike element (31) comprising a long and thin extension of the same impermeable and flexible material as the flexible body (2), wherein the threadlike element (31) is longer than the body and has a sufficient length in order that, once the hygienic device has been placed in the vagina of the body of the user, a distal end of said threadlike element (31) is capable of remaining externally located from the vagina of the body of the user.

2. The hygienic device for the collection of menstrual flow, according to claim 1, characterized in that the threadlike element (31) has a structure easily cut at one, two or more points (32), so that the user can cut the threadlike element (31) at will until leaving it with a minimum length.

3. The hygienic device for the collection of menstrual flow, according to the claim 2, characterized in that the threadlike element (31) has, at the proximal area, joining it to the lower part of the body (2) of the receptacle, at least one protrusion (33).

4. The hygienic device for the collection of menstrual flow, according to the claim 2, characterized in that the threadlike element (31) has, at the proximal area, joining it to the lower part of the body (2) of the receptacle, two protrusions (33) separated by a recess.

5. The hygienic device for the collection of menstrual flow, according to claim 1, characterized in that the distal end of the threadlike element (31) has a protrusion (33) to facilitate withdrawing the cup from the vagina after it is used.

6. The hygienic device for the collection of menstrual flow, according to claim 1, characterized in that, the upper part of the body (2) of the receptacle is provided with one or more holes (4) close to the edge of the mouthpiece (21).

7. The hygienic device for the collection of menstrual flow, according to claim 1, characterized in that, said flexible body (2) is formed of silicone.

* * * * *